United States Patent
Ali et al.

(10) Patent No.: US 9,309,336 B2
(45) Date of Patent: Apr. 12, 2016

(54) SYNTHESIS AND ANTISCALANT BEHAVIOR OF A NOVEL POLYZWITTERIONIC ACID

(71) Applicants: King Fahd University of Petroleum and Minerals, Dhahran (SA); King Abdulaziz City for Science and Technology, Riyadh (SA)

(72) Inventors: Shaikh Asrof Ali, Dhahran (SA); Shamsuddeen Abdullahi Haladu, Dhahran (SA)

(73) Assignees: King Fahd University Of Petroleum and Minerals, Dhahran (SA); King Abdulaziz City for Science and Technology, Riyadh (SA)

( * ) Notice: Subject to any disclaimer, the term of this patent is extended or adjusted under 35 U.S.C. 154(b) by 328 days.

(21) Appl. No.: 14/092,363

(22) Filed: Nov. 27, 2013

(65) Prior Publication Data

US 2015/0144162 A1 May 28, 2015

(51) Int. Cl.
| | | |
|---|---|---|
| *C08F 36/20* | (2006.01) | |
| *C07F 9/572* | (2006.01) | |
| *C07F 9/38* | (2006.01) | |
| *C07F 9/40* | (2006.01) | |
| *C09K 8/00* | (2006.01) | |
| *C02F 5/12* | (2006.01) | |

(52) U.S. Cl.
CPC . *C08F 36/20* (2013.01); *C02F 5/12* (2013.01); *C07F 9/3808* (2013.01); *C07F 9/4006* (2013.01); *C07F 9/5721* (2013.01); *C09K 8/00* (2013.01)

(58) Field of Classification Search
CPC .................. C02F 5/12; C11D 3/3796
See application file for complete search history.

(56) References Cited

U.S. PATENT DOCUMENTS

| | | | |
|---|---|---|---|
| 6,410,671 B1 | 6/2002 | Argillier et al. | |
| 7,300,990 B2 | 11/2007 | Lewis et al. | |
| 8,048,408 B2 | 11/2011 | Lewis | |
| 8,182,802 B2 | 5/2012 | Lewis et al. | |
| 8,906,972 B1 * | 12/2014 | Al-Hamouz | 210/636 |
| 8,937,104 B2 * | 1/2015 | Ali | C08G 75/205 521/28 |
| 9,120,094 B2 * | 9/2015 | Ali | B01J 41/14 |
| 2004/0063881 A1 * | 4/2004 | Lewis | C08F 4/40 526/258 |
| 2005/0159556 A1 * | 7/2005 | Lewis | C08F 4/40 525/280 |
| 2008/0045420 A1 * | 2/2008 | Karagianni | C08F 246/00 507/121 |
| 2014/0047653 A1 * | 2/2014 | Sherry | C08F 220/06 15/104.93 |
| 2014/0190895 A1 * | 7/2014 | Rahman | C02F 1/68 210/700 |
| 2015/0144162 A1 * | 5/2015 | Ali | C08F 36/20 134/41 |
| 2015/0144556 A1 * | 5/2015 | Ali | C02F 5/14 210/638 |
| 2015/0144569 A1 * | 5/2015 | Ali | C08G 75/24 210/698 |
| 2015/0174572 A1 * | 6/2015 | Ali | B01J 41/14 521/38 |
| 2015/0183933 A1 * | 7/2015 | Ali | B01D 65/02 210/636 |

* cited by examiner

*Primary Examiner* — Gregory Webb
(74) *Attorney, Agent, or Firm* — Oblon, McClelland, Maier & Neustadt, L.L.P.

(57) ABSTRACT

A zwitterionic monomer and corresponding cyclopolymerized polyzwitterion (±) (PZ) containing, on each repeating unit, both phosphonate and sulfonate functionalities. Phosphonate ester hydrolysis in PZ gave a pH-responsive polyzwitterionic acid (±) (PZA). The PZA under pH-induced transformation was converted into polyzwitterion/anion (±−) (PZAN) and polyzwitterion/dianion (±=) (PZDAN).

11 Claims, 9 Drawing Sheets

SYNTHESIS AND ANTISCALANT BEHAVIOR OF A NOVEL POLYZWITTERIONIC ACID

BACKGROUND OF THE INVENTION

1. Technical Field

The invention relates to a zwitterionic monomer, a polyzwitterion synthesized from the zwitterionic monomer, a pH-responsive polyzwitterionic acid synthesized from the polyzwitterion, a polyzwitterion/anion and polyzwitterion/dianon synthesized from the polyzwitterionic acid, and the corresponding methods by which each compound and polymer is formed and use of the polyzwitterionic acid as an antiscalant.

2. Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The polymers conventionally used in water-base fluids are acrylamide derivatives, generally acrylamide/acrylate copolymers obtained by copolymerization of acrylamide and acrylate or by polyacrylamide hydrolysis. They are however sensitive to the conditions of use that can be encountered. A high shear gradient and/or a high bottomhole temperature can lead to a decrease in molar mass and viscosifying power. Furthermore, they are sensitive to media with high ionic strength because of the presence of carboxylate or sulfonate groups which also lead to a loss of viscosifying power or even to a precipitation in media with high divalent ion concentrations.

For applications in saline media, polyampholytes carrying both positive charges and negative charges can be suitable. When the charges on the polymeric material are in equal number (neutral polyampholytes) and proton exchange is suppressed, the properties in aqueous solution of these materials are governed by the attractive forces that exist between the unlike charges of the polyampholyte. They are generally more soluble and have higher viscosities in a saline medium than in deionized water. The behaviour of this type of polymer is therefore referred to as antipolyelectrolyte behaviour.

In the case of polyampholytes that do not have the same number of positive and negative charges, according to the extent of the excess of one charge type in relation to the other, the polyelectrolyte effect or the neutral polyampholyte effect characterizes behaviour in solution.

These polyampholytes are already used in many applications, in particular for the formulation of cleaning compounds and cosmetic applications, the latter depending on the nature of the zwitterion, composition of the polymer and on the molar mass of the polymer.

Butler's cocyclopolymerization protocol (G. B. Butler, "Cyclopolymerization and cyclocopolymerization," Marcel Dekker: New York, 1992; S. Kudaibergenov et al., *Advances in Polymer Science*, 2006, 201, 157-224; P. K. Singh, et al., *e-Polymers*, 2007, 030, 1-34; W. Jaeger, et al., "*Prog. Polym. Sci.*," 2010, 35, 511-577—each incorporated herein by reference in its entirety) involving N,N-diallyl quaternary ammonium salts has generated a plethora of industrially significant water-soluble cationic polyelectrolytes. Use of ammonio monomers $[(CH_2=CH-CH_2)_2NH^+R-Y^-]$ having unquenched nitrogen valency and pendent (R) bearing carboxylate, phosphonate or sulfonate functionalities ($Y^-$) have provided entries into polymers which can participate in pH-induced equilibrations involving cationic (+), anionic (−), zwitterionic (±) and ampholytic (+−) centers in the repeating units (H. A. Al-Muallem, et al., *Polymer*, 2002, 43, 4285-4295; S. A. Ali, et al., *J. Polym. Sci. Part A: Polym. Chem*, 2003, 41, 172-184; O. C. S. Al-Hamouz, et al., *J. Polym. Sci. Part A Polym chem*, 2012, 50, 3580-3591; N.Y. Abu-Thabit, et al., *J. Appl. Polym. Sci.*, 2011, 120, 3662-3673—each incorporated herein by reference in its entirety). Bio-mimicking polyampholytes and polyzwitterions, have also offered many new applications in biotechnology, medicine, oil industry, and hydrometallurgy.

While the cationic or anionic polyelectrolytes demonstrate polyelectrolyte behavior, i.e. their viscosity is diminished upon addition of electrolytes (e.g. NaCl), the polyzwitterions (PZs) show anti-polyelectrolyte behavior of enhanced viscosity and solubility as a result of globule-to-coil transition. The transition is an outcome of salt-induced disruption of intragroup, intrachain and interchain ionic cross-links (J. C. Salamone, et al., *Polymer*, 1978; 19, 1157-1162; T. A. Wielema, et al., *Eur. Polym. J.*, 1987, 23, 947-950; P. G. Higgs, et al., *J. Chem. Phys.*, 1991, 94, 1543-1554; M. Skouri, et al., *Macromolecules*, 1994, 27, 69-76—each incorporated herein by reference in its entirety).

Antiscalants are chemical substances that inhibit the formation of scales which is a nuisance in the operation of water desalination plants (R. J. Davey, *The Role of Additives in Precipitation Processes*, Industrial Crystallization 81, Eds. S. J. Jancic and E. J. de Jong, North-Holland Publishing Co., 1982, 123-135—incorporated herein by reference in its entirety). Calcium sulfate and calcium carbonate are primary contributors to scale formation. Scale deposits, which are generated and extended mainly by means of crystal growth, can be inhibited by modification of its growth and dispersion of the scale forming minerals. Various polyelectrolytes, which are usually added to saline water in substoichiometric amounts, are adsorbed onto the surfaces of the crystals so as to inhibit further crystal growth. A mixture of 90:10 copolymer of acrylic acid/$(CH_2=CH-CH_2)_2N^+(Me)CH_2CH_2SO_3^-$ and 2-phosphono butane 1,2,4-tricarboxylic acid (PBTA) has been reported (D. W. Fong, et al., U.S. Pat. No. 6,225,430 B1, May, 2001—incorporated herein by reference in its entirety) to perform better scale inhibition than poly(acrylic acid) (PAA) alone or a mixture of PAA and PBTA.

When the monomer which represents repeating units of the polymer contains exactly one an ammonium group and a matching anionic group, it belongs to the betaine family and the charges form an inner salt. A distinctive feature of the polymers of the invention is that the unlike charges are of the betaine type and are thus electrically neutral polymers. The positive charge is provided by a quaternary ammonium function, the negative charge by a sulfonate (sulfobetaines) or phosphonate (phosphobetaines) group.

Some copolymers were obtained by copolymerization of acrylamide with carboxybetaine type monomers. Their properties in solution greatly depend on the pH value and they are incompatible with the desired properties. In fact, at a low pH value, the protonation of the carboxylate functions leads to the loss of the zwitterionic character and the copolymer behaves like a cationic polyelectrolyte, thus sensitive to the presence of salt in particular.

The polybetaines described here have the advantage of keeping their zwitterionic character within a wide pH range. Certain acrylaride and sulfobetaine copolymers have already been described, but they result from synthesis processes carried out in the presence of salts, which is of notable importance for the structures obtained.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

One embodiment of the invention includes a zwitterionic monomer.

Another embodiment includes a method for synthesizing and copolymerizing the zwitterionic monomer to form a polyzwitterion (±) (PZ) containing on each repeating unit both phosphonate and sulfonate functionalities.

Another embodiment includes a method in which hydrolysis of the phosphonate ester in the (±) (PZ) forms a pH-responsive polyzwitterionic acid (±) (PZA).

Another embodiment includes a method in which the (±) PZA undergoes pH-induced transformation and is converted into polyzwitterion/anion (+−) (PZAN) and polyzwitterion/dianion (±=) (PZDAN).

Another embodiment includes using the (±) PZA as an antiscalant in a Reverse Osmosis desalinization plant to inhibit or treat the formation of a scale.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
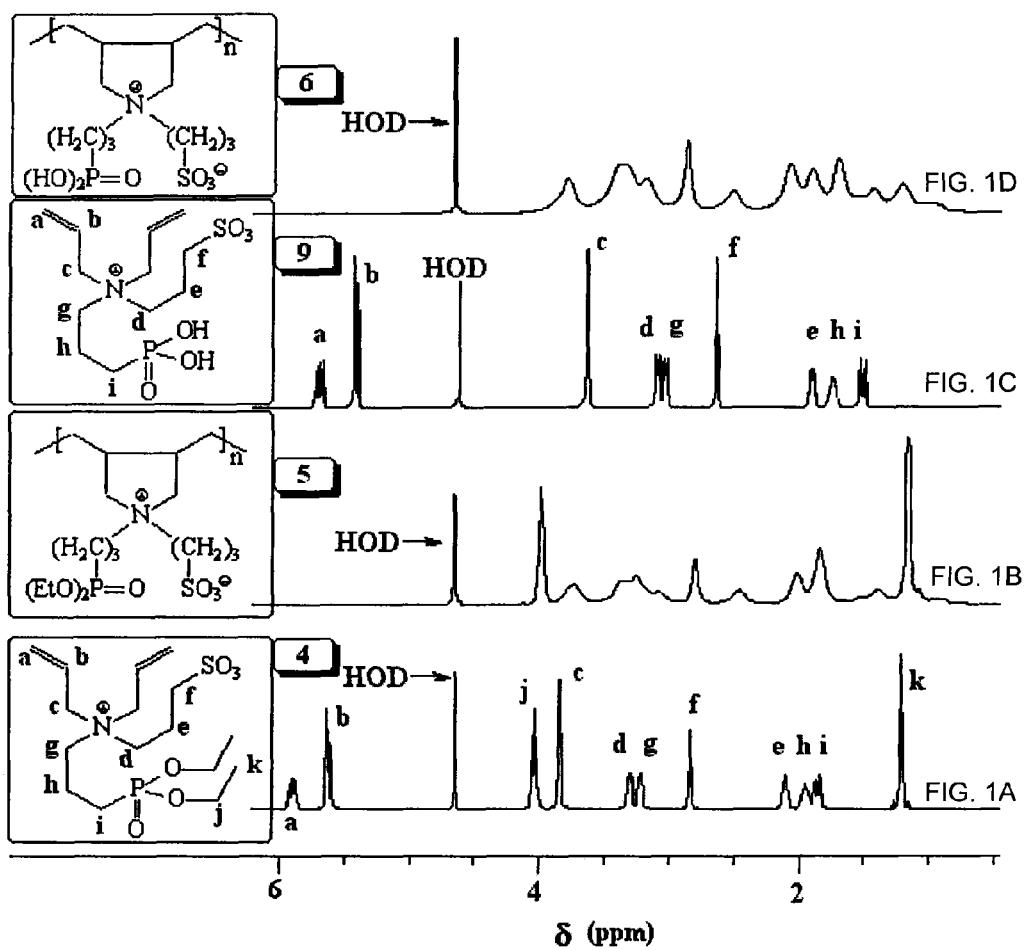
FIGS. 1A-1D show $^1$H NMR spectra of the corresponding polymers in (+NaCl) in $D_2O$.

The invention includes the zwitterionic monomer 4 having the following structure (I):

Zwitterionic monomer 4 of formula (I) is a cationic nitrogen-containing compound bonded to two allyl units. is The nitrogen atom is further bonded to Phospho- and Sulfopropyl a groups the formula for each phosphonate group being (—P(O)(OH)$_2$ or —P(O)(OR)$_2$) where the "R" group may be the same or different and is preferably a $C_1$-$C_6$ alkyl or $C_6$-$C_{12}$ aryl group selected from the group consisting of methyl, ethyl, propyl, butyl, pentyl, or hexyl or the aryl groups consisting of phenyl, tolyl, xylyl, mesityl, naphthyl, biphenyl and any isomers thereof. "R" may be substituted or unsubstituted. Preferably the "R" group of the phosphonate group is an ethyl group.

The synthesis of a specialty zwitterionic monomer 4 and its corresponding cyclopolymer (±) 5 where the phosphonate ester functionality offers latitude for chemical transformation to a poly(zwitterions/anion) (±−) 7 and poly(zwitterions/dianion) 8 (±=) are presented in Scheme 1. The polymers 5-8 having different charges on the polymer backbone but identical degree of polymerization permit a reasonable comparison and correlation of their solution properties with the charge types and densities on the polymer backbone (M. A. J. Mazumder, et al., *Polymer* 2004, 45, 125-132; M. M. Ali, et al., *Polymer* 2000, 41, 5591-5600—each incorporated herein by reference in its entirety). Cyclocopolymer 8 is a cyclopolymer having phosphonate and sulfonate functionalities in the same repeating unit. The tribasic repeating unit having different $pK_a$ values permits the change of the charge type by adjusting the pH.

SCHEME 1 Cyclopolymers via Butler's cyclopolymerization protocol.

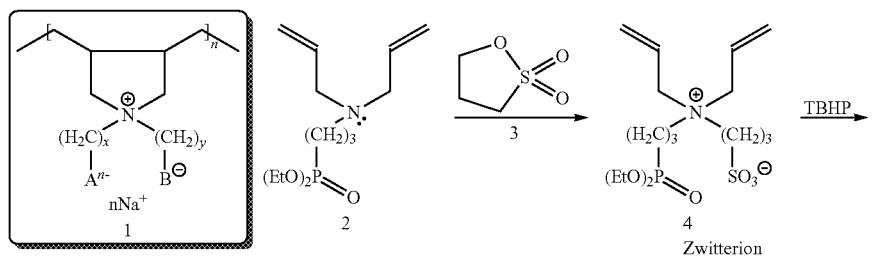

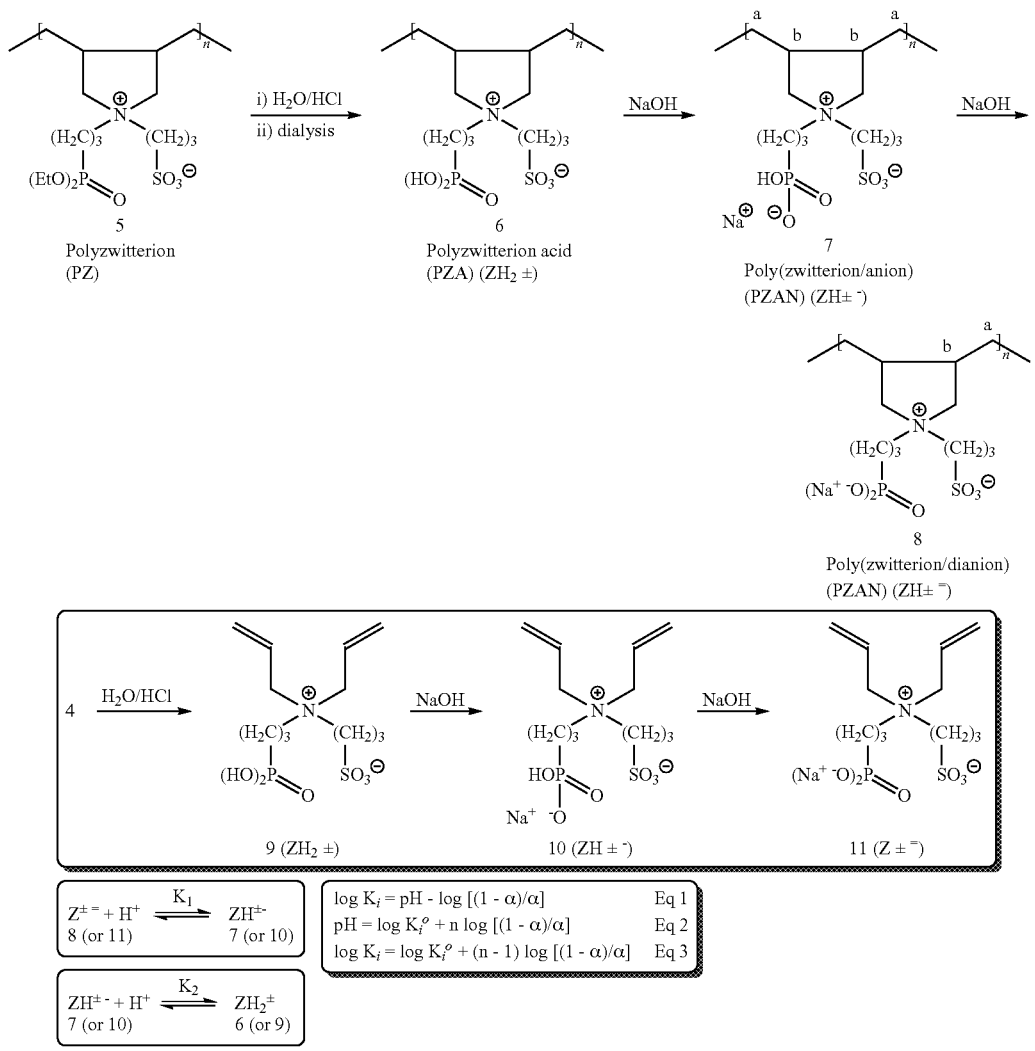

As depicted in Scheme 1, a polymer 1 serves as a generic model for the polymers polyzwitterion (PZ) 5, polyzwitterionic acid (PZA) ($ZH_2^\pm$) 6, poly(zwitterion/anion) (PZAN) ($ZH^{\pm-}$) 7, and poly(zwitterion/dianon) (PZDA) ($Z^{\pm=}$) 8 that are formed from zwitterionic monomer 4. Polymer 1 has the following structure:

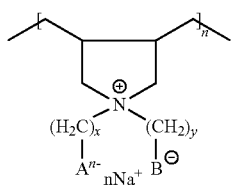

Polymer 1 includes repeating units of a five-membered heterocyclic ring having a nitrogen atom bonded to a linking unit comprising a phosphonate group ($A^{n-}$) with the formula for each phosphonate group being (—P(O)(OH)$_2$ or —P(O)(OR)$_2$) where the "R" group is preferably an alkyl or aryl group selected from the group consisting of methyl, ethyl, propyl, butyl, pentyl, or hexyl or aryl groups selected from the group consisting of phenyl, tolyl, xylyl, mesityl, naphthyl, biphenyl and any isomers thereof "R" may be substituted or unsubstituted. Preferably the "R" group of the phosphonate group is an ethyl group. The phosphonate group and linking groups can be further represented in polymer 1 as —(CH$_2$)$_x$-$A^{n-}$. More specifically, the variable "x" represents the number of methylene units, and "x" is 3. The group "$A^{n-}$" represents a phosphonate group. Variable "$n^-$" represents the charge value of the corresponding phosphonate group and also the coefficient representing the number of atoms of the cationic counter ion. The "n" represents the number of repeating units of the corresponding polymer and "n" is at least 10, preferably at least 15, 20, 40, 80, or 100. More preferably, "n" is in the range of 20-1,500; 40-1,400; 80-1,300; or 100-1,200. Cationic materials such as $K^+$, $Cu^+$, or $Li^+$ and dicationic materials such as $Ca^{2+}$, $Cr^{2+}$, $Cu^{2+}$, $Fe^{2+}$, $Pb^{2+}$, $Mg^{2+}$, $Mn^{2+}$, $Hg^{2+}$, $Sr^{2+}$, $Sn^{2+}$, or $Zn^{2+}$ may be used in place of $Na^+$.

The nitrogen atom included in the five-membered heterocyclic ring is also bonded to a linking unit comprising a sulfonate group with the formula (—SO$_3$). The sulfonate group and linking groups can be further represented in polymer 1 as —(CH$_2$)$_y$—$B^-$ in polymer 1. The variable "y" represents the number of methylene units, and "y" is 3. The variable "B" represents the sulfonate group.

As further depicted in Scheme 1 above, a solution of the monomer 2, which is a tertiary amine, e.g., diethyl 3-(diallylamino)propylphosphonate, is treated with a cyclic sulfonate ester of a hydroxy sulfonic acid 3, more preferably in the form of propane sultone to yield a monomeric zwitterion 4. The treatment of monomer 2 with ester 3 yields the resultant anionic sulfonate material and thus balances the cationic charge of the nitrogen atom of the 5-membered heterocyclic ring. The monomeric zwitterion 4 is the monomer 3-[diallyl{3-(diethoxyphosphoryl)propyl}ammonio]propane-1-sulfonate. The monomer is a cationic nitrogen-containing compound bonding to units where the phosphoryl group consists of the formula, e.g., —$CH_2$—P(O)(OR)$_2$ where the "R" group is preferably an alkyl group selected from the group consisting of methyl, ethyl, propyl, butyl, pentyl, or hexyl or an aryl group selected from the group consisting of phenyl, tolyl, xylyl, mesityl, naphthyl, biphenyl and any isomers thereof. Preferably the "R" group of the phosphonate group is an ethyl group.

The monomeric zwitterion 4 is then treated with a polymerizing agent such as a peroxide solution, more preferably a tert-butyl hydroperoxide solution (TBHP), which acts to initiate cyclopolymerization of the zwitterionic monomer 4 to yield a polyzwitterion 5. The polyzwitterion 5 contains the core structure following the model of polymer 1, further including the phosphoryl group with the formula —$CH_2$—P(O)(OR)$_2$ where the "R" group is preferably an alkyl group selected from the group consisting of methyl, ethyl, propyl, butyl, pentyl, or hexyl or the aryl groups consisting of phenyl, tolyl, xylyl, mesityl, naphthyl, biphenyl and any isomers thereof. Preferably the "R" group of the phosphonate group is an ethyl group.

The polyzwitterion 5 then undergoes a two stage reaction in which a first stage includes a solution of PZ 5 in water and a concentrated inorganic acid, more preferably HCl, and a second stage of dialysis to yield a polyzwitterionic acid (PZA) ($ZH_2^\pm$) 6, which contains two hydroxy groups in the formula of the phosphonate group. (PZA) ($ZH_2^\pm$) 6 contains the structure following the model of polymer 1, further including the phosphonate group in the form of C—P(O)(OH)$_2$. Polyzwitterionic acid 6 is used as an antiscalant in reverse osmosis plants against mineral scales and/or deposits such as $CaCO_3$, $CaSO_4$, $Mg(OH)_2$.

Treatment of (PZA) ($ZH_2^\pm$) 6 with an alkaline material, e.g., NaOH, KOH, Ca(OH)$_2$ and the like, deprotonates one of the hydroxy groups of the phosphonate group to provide a polymeric material having an anionic charge. The anionically charged derivative of the of (PZA) ($ZH_2^\pm$) 6 is shown as poly(zwitterion/anion) (PZAN) ($ZH^{\pm-}$) 7.

Upon further treatment of (PZAN) ($ZH^{\pm-}$) 7 with additional base, the anionic oxygen atom of the phosphonate group forms a ($Na^+$-O) complex bonded to the phosphorus atom to yield a dianionic charge. The dianionically charged derivative of the (PZAN) ($ZH^{\pm-}$) 7 is shown as poly(zwitterion/dianon) (PZDA) ($Z^{\pm=}$) 8.

Both (PZAN) ($ZH^{\pm-}$) 7 and (PZDA) ($Z^{\pm=}$) 8 may also be used as antiscalants in reverse osmosis plants against mineral scales such as $CaCO_3$, $CaSO_4$, $Mg(OH)_2$.

Further, treatment of polyzwitterion 8 with a solution of $H_2O$ and HCl gives the monomer ($ZH_2^\pm$) 9. Treatment of ($ZH_2^\pm$) 9 with an alkaline material, e.g., NaOH, KOH, Ca(OH)$_2$ and the like deprotonates one of the hydroxy groups of the phosphonate group to provide a monomeric material having an anionic charge. The anionically charged derivative of the of the ($ZH_2^\pm$) 9 is shown as monomer 10 ($ZH^{\pm-}$), which is the corresponding monomer to (PZAN) ($ZH^{\pm-}$) 7.

Upon further treatment of 10 ($ZH^{\pm-}$) with additional base, the anionic oxygen atom of the phosphonate group forms a ($Na^+$-O)$_2$ complex bonded to the phosphorus atom to yield a dianionic charge. The dianionically charged derivative of the 10 ($ZH^{\pm-}$) is shown as monomer 11 ($Z^{\pm\pm}$), which is the corresponding monomer to (PZDA) ($Z^{\pm=}$) 8.

Synthesis of 3-[Diallyl{3-(diethoxyphosphoryl)propyl}ammonio]propane-1-sulfonate (4) preferably occurs by the following method: under $N_2$ at 70° C., a solution of diethyl 3-(diallylamino)propylphosphonate 2 (15.0 g, 54.5 mmol) and 3 (7.0 g, 57.3 mmol) in $CH_3CN$ (30 cm$^3$) was stirred for 60 h. The residue, after removal of acetonitrile, was crystallized from acetone (30 cm$^3$) in the presence of small amount of methanol to give white crystals of 4 (19.5 g, 90%). The extremely hygroscopic monomer is insoluble in acetone but soluble in methanol or water. Mp 140-142° C. (closed capillary); (Found: C, 47.9; H, 8.4; N, 3.4; S, 7.8%. $C_{16}H_{32}NO_6PS$ requires C, 48.35; H, 8.11; N, 3.52; S, 8.07%); $v_{max}$ (KBr): 3402, 2985, 2940, 1644, 1479, 1428, 1394, 1213, 1042, 967, 875, 786, 733 and 605 cm$^{-1}$; $\delta_H$ ($D_2O$) 1.22 (6H, t, J=7 Hz), 1.86 (2H, m), 1.96 (2H, m), 2.11 (2H, m), 2.84 (2H, t, J=7.5 Hz), 3.23 (2H, apparent t, J=10 Hz), 3.31 (2H, apparent t, J=10 Hz), 3.85 (4H, d, J=7 Hz), 4.04 (4H, m), 5.64 (4H, m), 5.89 (2H, m), (HOD: 4.65); $\delta_C$ ($D_2O$) 15.83 (s, $PCH_2$$CH_2$), 16.47 (d, 2C, Me, $^3$J (PC) 4.1 Hz), 18.29 (s, $SCH_2$$CH_2$), 21.45 (d, $PCH_2$, $^1$J (PC) 143 Hz), 47.97 (s, $SCH_2CH_2CH_2$), 57.26 (s, $SCH_2CH_2CH_2$), 58.32 (d, PCH2CH2$CH_2$, $^3$J (PC) 16.4 Hz), 61.72 (2C, =CH—$CH_2$, s), 64.38 (d, 2C, O$CH_2$CH$_3$, $^2$J (PC) 6.2 Hz), 124.40 (2C, s, $CH_2$=$CH$), 129.80 (2C, s, $CH_2$=CH) (dioxane: 67.40 ppm); $\delta_P$ (202 MHz, $D_2O$): 31.01 (s). DEPT 135 NMR analysis was carried out to assign the $^{13}$C signals.

Figure 2:
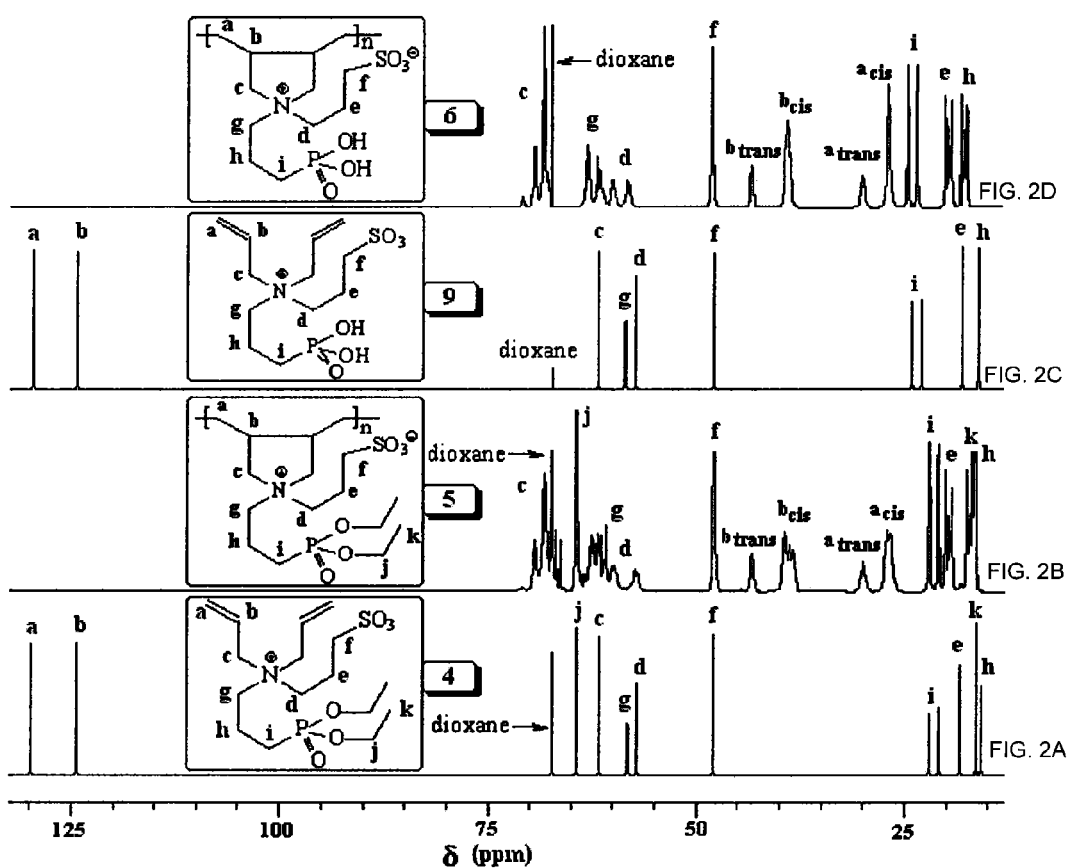
FIGS. 2A-2D show $^{13}$NMR spectra of the corresponding polymers in (+NaCl) in $D_2O$.
Figure 3:
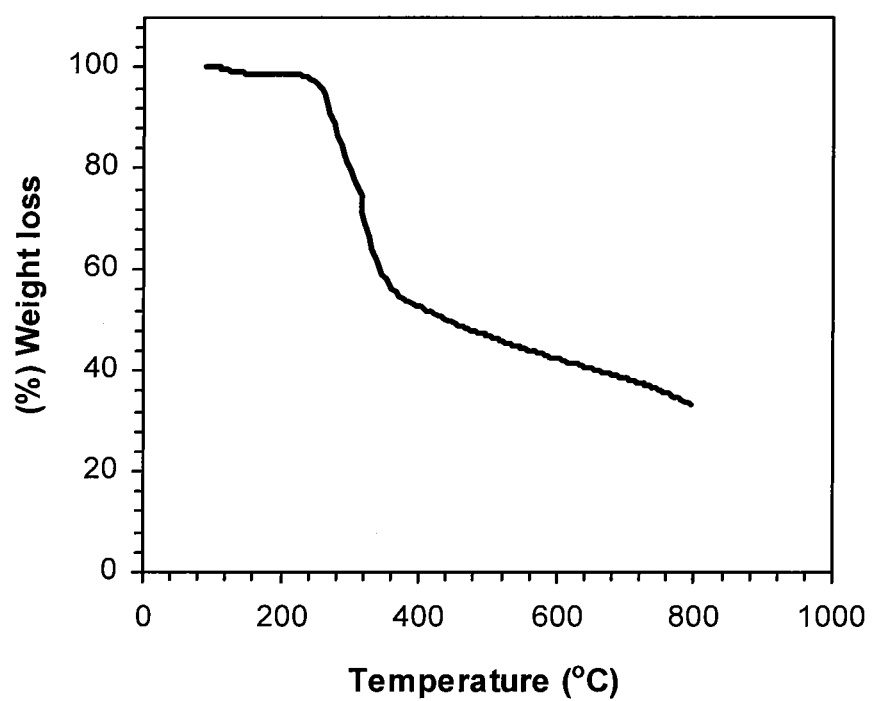
FIG. 3 shows a TGA curve of PZ 5.

The cyclopolymerization of the monomer 4 preferably occurs by the following method: A solution of monomer 3 (7.94 g, 20 mmol), 1 N NaCl (2.64 g) and TBHP (60 mg) under $N_2$ was stirred in a closed 25-cm$^3$ round-bottom flask at 90° C. for 24 h (Table 1, entry 3). Upon dialysis (24 h) of the resultant polymer against deionized water followed by freeze-drying afforded PZ 5 as a white polymer. Thermal decomposition: the color became dark brown at 270° C. and decomposition happened at 320° C. (Found: C, 48.0; H, 8.3; N, 3.4; S, 7.7%. $C_{16}H_{32}NO_6PS$ requires C, 48.35; H, 8.11; N, 3.52; S, 8.07%); $v_{max}$. (KBr) 3407, 2985, 2941, 1650, 1463, 1395, 1370, 1214, 1044, 969, 789, 734 and 604 cm$^{-1}$. $\delta_P$ (202 MHz, $D_2O$): 31.13. FIGS. 2 and 3 show the respective $^1$H NMR and $^{13}$C NMR spectra.

Conversion of PZ 5 to PZA 6 preferably occurs by the following method: A solution of PZ 5 (3.0 g, 7.5 mmol) (derived from entry 3, Table 1) in water (18 mL) and concentrated HCl (24 mL) and was heated in a flask at 90-95° C. for 24 h or until the ester hydrolysis was complete. Insoluble polymer started to precipitates out within 1 h during dialysis (24 h) of the homogeneous mixture against water. The insoluble polymer started to redissolve after 3 h. The solution of the polymer was freeze dried to obtain PZA 6 as a white solid (2.5 g, 98%). Thermal decomposition: dark brown at 300° C. and black at 325° C. (Found: C, 41.9; H, 7.3; N, 4.0; S, 9.1%. $C_{12}H_{24}NO_6PS$ requires C, 42.22; H, 7.09; N, 4.10; S, 9.39%); $v_{max}$ (KBr) 3449 (br), 2942, 1653, 1465, 1417, 1216, 1043, 984, 938, 786, 732, and 610 cm$^{-1}$. $\delta_P$ (202 MHz, $D_2O$): 25.35. FIGS. 1 and 2 display the $^1$H and $^{13}$C NMR spectra, respectively.

Acid hydrolysis of 4 zwitterion acid ZA 9 preferably occurs by the following method: A solution of Z 4 (2.7 g, 6.8 mmol) in water (5.5 mL) and concentrated HCl (4.8 mL) was heated in a flask at 95° C. for 48 h. Removal of the solvent followed by dissolution of the residual liquid in methanol, and precipitation into acetone gave ZA 9 as a white solid (dried under reduced pressure at 50° C.) (2.1 g, 91%). Mp. 75-80° C. (Found: C, 41.8; H, 7.3; N, 3.9; S, 9.1%. $C_{12}H_{24}NO_6PS$ requires C, 42.22; H, 7.09; N, 4.10; S, 9.39%); $\nu_{max}$ (KBr) 3600-2500 (very broad), 1699, 1642, 1477, 1430, 1373, 1221 (br), 1163, 1041, 1001, 952, 870, 784, 732, 602 and 526 cm$^{-1}$. $\delta_H$ (D$_2$O) 1.55 (2H, dt, J=18.4 and 7.6 Hz), 1.77 (2H, m), 1.93 (2H, m), 2.11 (2H, m), 2.66 (2H, t, J=7 Hz), 3.04 (2H, m), 3.10 (2H, m), 3.66 (4H, d, J=7 Hz), 5.44 (4H, m), 5.73 (2H, m), (HOD: 4.65); $\delta_C$ (D$_2$O) 16.28 (s, PCH$_2$CH$_2$), 18.26 (s, SCH$_2$CH$_2$), 23.68 (d, PCH$_2$, $^1$J (PC) 138 Hz), 47.99 (s, SCH$_2$CH$_2$CH$_2$), 57.30 (s, SCH$_2$CH$_2$CH$_2$), 58.65 (d, PCH$_2$CH$_2$CH$_2$, $^3$J (PC) 18.6 Hz), 61.74 (2C, =CH—CH$_2$, s), 124.43 (2C, s, CH$_2$—CH), 129.73 (2C, s, CH$_2$=CH) (dioxane: 67.40 ppm); $\delta_P$ (202 MHz, D$_2$O): 28.02 (m). DEPT 135 NMR analysis was carried out to assign the $^{13}$C signals.

Conversion of ZA 9 to dianion/zwitterion 11 preferably occurs by the following method: A solution of ZA 9 (1.45 g g, 4.25 mmol) in methanol (2 mL) and NaOH (0.51 g, 12.7 mmol) in methanol (4 mL) was stirred at 23° C. for 2 min. The removal of the solvent followed by trituration of the residue with acetone/ether mixture afforded 11 as a white solid (1.4 g, 85%). Because of the extremely hygroscopic nature of the salt, its elemental analysis was not performed. Mp. Did not melt, brown at 300° C. and black at 330° C. $\nu_{max}$ (KBr) broad adsorption in the range 3600-2600, 1644, 1477, 1418, 1364, 1215, 1049, 976, 862, 735, and 606 cm$^{-1}$. $\delta_H$ (D$_2$O) 1.28 (2H, m), 1.83 (2H, m), 1.93 (2H, m), 2.13 (2H, m), 2.86 (2H, m), 3.19 (2H, m), 3.29 (2H, m), 3.83 (4H, d, J=7 Hz), 5.63 (4H, m), 5.93 (2H, m), (HOD: 4.65); $\delta_C$ (D$_2$O) 17.83 (d, PCH$_2$CH$_2$, $^2$J (PC) 15.0 Hz), 26.04 (d, PCH$_2$, $^1$J (PC) 210 Hz), 28.62 (s, SCH$_2$CH$_2$), 47.71 (s, SCH$_2$CH$_2$CH$_2$), 56.82 (s, SCH$_2$CH$_2$CH$_2$), 59.90 (d, PCH$_2$CH$_2$CH$_2$, $^3$J (PC) 33.4 Hz), 61.13 (2C, =CH—CH$_2$, s), 124.36 (2C, s, CH$_2$=CH), 129.10 (2C, s, CH$_2$=CH) (dioxane: 67.40 ppm); $\delta_P$ (202 MHz, D$_2$O): 17.41. DEPT 135 NMR analysis was carried out to assign the $^{13}$C signals.

Protonation constants ($K_1$ and $K_2$) of polymer 8 [ZH$_2^{\pm=}$] and its corresponding monomer unit 11 [ZH$_2^{\pm=}$] were determined by potentiometric titrations which were carried out in atmosphere of N$_2$ in CO$_2$-free water as described elsewhere using a solution (Tables 3 and 4) of PZDA 6 [ZH$_2^{\pm}$] or monomer form 11 [ZH$_2^{\pm=}$] in 200 cm$^3$ of salt-free water or 0.1 N NaCl (S. A. Ali, et al., *J. Polym. Sc. A: Polym. Chem.* 2010, 48, 5693-5703—incorporated herein by reference in its entirety). The Log $K_1$ and Log $K_2$ of the —P(=O)O$^=$ (in 8 or 11) are calculated at each pH value by the Henderson-Hasselbalch eq 2 (Scheme 1) where a is the ratio [ZH$^{\pm-}$]$_{eq}$/[Z]$_o$ and [ZH$_2^{\pm}$]$_{eq}$/[Z]$_o$, respectively. The [ZH$^{\pm-}$]$_{eq}$ and [ZH$_2^{\pm}$]$_{eq}$ represent the respective equilibrium concentrations of the first and second protonated species whereas [Z]$_o$ describes the initial concentration of repeating units.

For the determination of the second step protonation constant (log $K_2$) of —P(=O)(OH)O$^-$ (i.e. [ZH$^{\pm-}$]) using the titration of polymer 6 [ZH$_2^{\pm}$] with NaOH, [Z]$_o$ and [ZH$_2^{\pm}$]$_{eq}$ are related by [ZH$_2^{\pm}$]$_{eq}$=[Z]$_o$−C$_{OH^-}$−[H$^+$]+[OH$^-$], where C$_{OH^-}$ represent the added NaOH concentration. The equilibrium [H$^+$] and [OH$^-$] values were calculated from the pH value (W. K. Felty, *J. Chem. Educ.* 1978, 55, 576; R. Barbucci, et al., *Macromolecules* 1981, 14, 1203-1209—each incorporated herein by reference in its entirety). The first step protonation constant (log $K_1$) involving the protonation of —P(=O)(O$^-$)$_2$ (i.e. [Z$^{\pm=}$]) using volume of the titrant after deducting the equivalent volume from the total volume. In this case, $\alpha$ represents the ratio [ZH$^{\pm-}$]$_{eq}$/[Z]$_o$ whereby [ZH$^{\pm-}$]$_{eq}$ equals [Z]$_o$−C$_{OH^-}$−[H$^+$]+[OH$^-$]. For the titration of 11 [Z$^{\pm=}$] with HCl, the protonated species' concentration is given by: [ZH$_{i=1,2}$]$_{eq}$=C$_H^+$−[H$^+$]+[OH$^-$].

Eq. 3 (Scheme 1) describes the apparent basicity constants of —P(=O)(O$^-$)$_2$ where log $K^o$=pH at $\alpha$=0.5 and n=1 in the case of sharp basicity constants.

The 'n' and log $K^o$ as the respective slope and intercept were determined from the linear regression fit of pH vs. log [(1−$\alpha$)/$\alpha$)]. Protonation at the same time of the three basic sites: —PO$_3^=$ (log $K_1 \approx$+8), —PO$_3$H$^-$ (log $K_2 \approx$+3) and —SO$_3^-$ (log $K_3 \approx$−2.1) (J. P. Guthrie, Can. J. Chem. 1978, 56, 2342-2354—incorporated herein by reference in its entirety) is not likely due to differences of their basicity constants by about 5 orders of magnitude (vide infra). Note that basicity constant log K of any base B is the p$K_a$ of its conjugate acid BH$^+$.

Zwitterion monomer 4, obtained in excellent yield by reacting tertiary amine 2 with propane sultone 3, underwent cyclopolymerization to afford polyzwitterion (PZ) 5 in very good yields (Scheme 1). The results, given in Table 1, revealed that the polymer under entry 3 using 3 mg initiator/mmol monomer has higher intrinsic viscosity [η] than that obtained with an initiator concentration of 4 mg/mmol monomer in a 1 M NaCl solution at 90° C. (entry 1). Note that the presence of salt (NaCl) is a requirement to obtain the polymer; in its absence only a trace amount of the polymer could be obtained (entry 2). The interesting beneficial influence of NaCl on the polymer yields could be attributed to the expansion of the collapsed coil zwitterionic macroradical. The presence of salt disrupts the zwitterionic interactions thereby forcing out the cocooned radical-head so as to have easier access to the monomer molecules for further propagation in a collapsed coil.

The PZ ($\pm$) 5 was hydrolyzed in 5.6 M HCl to give PZA ($\pm$) 6, which on neutralization with 1 and 2 equivalents of NaOH is expected to generate polyzwitterion/anion (PZAN) ($\pm$−) 7 and polyzwitterion/dianion (PZDAN) ($\pm$=) 8. Likewise, the zwitterion monomer 4 was hydrolyzed to zwitterion acid 9 which on neutralization with NaOH afforded the zwitterion/dianion 11.

TABLE 1

Cyclopolymerization[a] of Monomer 4

| Entry No. | Monomer (mmol) | Initiator (mg) | NaCl (M) | Yield (%) | [η][b] (dL g$^{-1}$) | $\overline{M}_W$ | (PDI)[c] |
|---|---|---|---|---|---|---|---|
| 1 | 10 | TBHP (40) | 1.00 | 80 | 0.0741 | 35.3 × 10$^3$ | 2.1 |
| 2 | 10 | TBHP (40) | 0 | trace | — | | |
| 3 | 20 | TBHP (60) | 1.00 | 76 | 0.0969 | 43.7 × 10$^3$ | 2.3 |

[a]Carried out using 75 w/w % monomer 4 (10 mmol) solution in the presence of tert-butyl hydroperoxide (TBHP) at 90° C. for 24 h.
[b]Viscosity of 1-0.125% polymer solution in 0.1 M NaCl was measured with Ubbelohde Viscometer (K = 0.005718) at 30° C.
[c]Polydispersity index.

PZ 5 or PZA 6 (2 w/w % mixture) in a solvent was stirred at 70° C. (1 h) and then brought back to 23° C. The solubility behaviors are given in Table 2.

TABLE 2

Solubility[a] of PZ 5 and PZA 6

| Solvent | ε | PZ 5 | PZA 6 |
|---|---|---|---|
| Formamide | 111 | + | + |
| Water | 78.4 | + | + |
| Formic acid | 58.5 | + | + |
| DMSO | 47.0 | − | + |

TABLE 2-continued

Solubility[a] of PZ 5 and PZA 6

| Solvent | ε | PZ 5 | PZA 6 |
|---|---|---|---|
| Ethylene glycol | 37.3 | − | + |
| DMF | 37.0 | − | − |
| Methanol | 32.3 | − | + |
| Triethylene glycol | 23.7 | − | + |
| Acetic acid | 6.15 | − | + |

[a] '+' indicates soluble and '−' indicates insoluble.

To a solution of PZA 6 (32 mg, 0.0937 mmol) in 0.730 M HCl (3.40 mL) was titrated with water until cloudiness. The first appearance of cloud required addition of water (4.00 mL). That means the polymer (0.013 M) is insoluble in the presence of 0.335 M HCl. Continued addition of water (13.4 mL) leads to disappearance of the cloudy mixture to colorless solution. That translates into the solubility of the polymer (0.00450 M) in 0.119 M HCl.

While PZA 6 was soluble in almost all the tested solvents, PZ 5 was soluble only in the protic solvents of higher dielectric constants (Table 2). Even though PZs are usually insoluble in salt-free water (R. S. Armentrout, et al., "Macromolecules," 2000, 33, 419-424; S. A. Ali, et al., "J. Polym. Sci. Part. A: Polym. Chem.," 2003, 41, 172-184. —each incorporated herein by reference in its entirety), the water-solubility of the current polymers is not unusual since a considerable number of polycarbobetaines, polysulfobetaines (PSB) have been documented to be soluble in salt-free water (S. A. Haladu, et al., *Eur. Polym. J*, 2013, 49, 1591-1600; S. A. Ali, Aal-e-Ali, *Polymer* 2001, 42, 7961-7970; S. A. Ali, et al., Polymer 1999, 40, 2439-2446; D. J. Walsh, et al., *Polymer* 1984, 25, 499-502—each incorporated herein by reference in its entirety). Water-insoluble PZs have been shown to be water-soluble with the assistance of NaCl which screens the zwitterionic charges from displaying zwitterionic interactions. Steric factor (V. M. Monroy Soto, et al., *Polymer* 1984, 25, 254-262—incorporated herein by reference in its entirety). around the crowded cationic charges in PZ 5 and 6, makes it difficult for the sulfonate group to move closer to impart effective zwitterionic interactions, thereby making them water-soluble.

Interestingly it was observed during the dialysis of PZA 6 in 5.6 M HCl, precipitation of the polymer happened within 1 h and its dissolution after 3 h. On further investigation it was revealed that a 5 wt % PAZ 6 forms a heterogeneous mixture in neutral water, while became soluble when diluted to 2%. It was calculated based on the pKa value of $-PO_3H_2$ of 3.26, the PZA 6 will be dissociated to the extent of 6 and 9% in 5 wt % and 2 wt % solution respectively in salt-free water. Greater dissociation thus makes the polymer soluble in the latter medium. A solution of PZA 6 (32 mg, 0.0937 mmol) in 0.730 M HCl (3.40 mL) was titrated with water until cloudiness. The first appearance of the cloud required the addition of water (4.00 mL). That means the polymer (0.013 M) is insoluble in the presence of 0.335 M HCl. Continued addition of water (13.4 mL) leads to disappearance of the cloudy mixture to colorless solution. That translates into the solubility of the polymer (0.00450 M) in 0.119 M HCl. The above results can be rationalized in terms of the equilibria presented in Scheme 2.

SCHEME 2 PZA 6 under pH-induced equilibrtion.

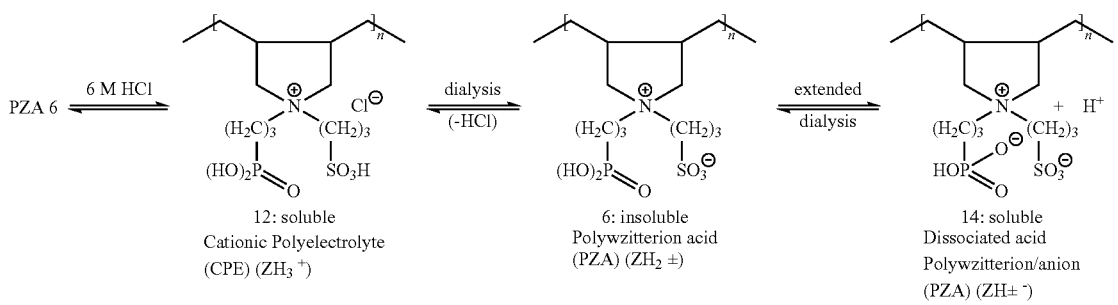

Scheme 2 describes the effect of (PZA) ($ZH_2^\pm$) 6 under pH-induced equilibration. For example, the reaction of (PZA) ($ZH_2^\pm$) 6 with an inorganic acid or an organic acid such as HCl. HBR, HI or $H_2SO_4$, more preferably the acid being HCl, results in a soluble cationic polyelectrolyte (CPE) ($ZH_3^+$) 12, in which the sulfonate group of the (PZA) ($ZH_2^\pm$) 6 is protonated to yield a sulfonic acid that is connected to the five-membered heterocyclic ring through an alkylene group. Further, dialysis of (CPE) ($ZH_3^+$) 12 deprotonates the sulfonic acid and regenerates the (PZA) ($ZH_2^\pm$) 6. Extended dialysis without the presence of HCl yields a soluble dissociated acid polyzwitterion/anion (PZA) ($ZH^{\pm-}$) 14, in which the one of the hydroxy groups of the phosphonate group is deprotonated to provide a polymeric material having an anionic charge.

Undissociated PZA 6 by virtue of being zwitterionic is insoluble in neutral water, however in the presence of concentrated HCl, it is converted to some extent into the soluble cationic polyelectrolyte (CPE) 12 which upon extended dialysis was transformed to a water-insoluble undissociated PZA 6 with the depletion of HCl. Continued dialysis in the absence of HCl encourages the participation of the dissociated acid in the equilibrium to give PZAN 14 whose water solubility is dictated by the anionic portion of the zwitterion/anion groups. Note that increased dilution will lead to greater solubility as the degree of dissociation of a weak acid is increased with decreasing concentration.

Referring now to the drawings, wherein like reference numerals designate identical or corresponding parts throughout the several views.

FIGS. 1A-1D illustrate the $^1$H NMR spectrum of (FIG. 1A) zwitterion monomer 4, (FIG. 1B) polyzwitterion 5, (FIG. 1C) monomer ($ZH_2^\pm$) 9 and (FIG. 1D) polyzwitterionic acid (PZA) ($ZH_2^\pm$) 6 (+NaCl) in $D_2O$. FIGS. 2A-2D illustrate the $^{13}$NMR spectrum of (FIG. 2A) zwitterion monomer 4, (FIG. 2B) polyzwitterion 5, (FIG. 2C)) monomer (ZH$_2^\pm$) 9 and (FIG. 2D) (PZA) (ZH$_2^\pm$) 6 (+NaCl) in D$_2$O. The IR adsorptions around ~1215 cm$^{-1}$ and ~1045 cm$^{-1}$ indicates the presence of sulfonate and phosphonate groups in the monomers and polymers. FIGS. 1A-1D and FIGS. 2A-2D show the $^1$H and $^{13}$C NMR spectra of 4, 5, 6, and 9, respectively. The DEPT 135 NMR analysis supported the assignments of the $^{13}$C signals. The termination via chain transfer and/or coupling process (R. M. Pike, et al., *J. Polym. Sci.* 1960, 44, 531-538; G. B. Butler, et al., *J. Am. Chem. Soc.*, 79, 3128 (1957)—each incorporated herein by reference in its entirety) is ascertained by the complete disappearance of any alkene proton or carbon signals in the polymer spectra. The absence of the ester group (OCH$_2$CH$_3$) signals in the spectra of 5 and 9 indicates its complete removal by hydrolysis. The integration of the $^{13}$C peaks revealed a 75/25 cis-trans ratio of the ring substituents at C$_{b,b}$ similar to the earlier findings (V. D. Vynck, et al., *Macromol. Rapid. Commun.* 1997, 18, 149-156; J. E. Lancaster, et al., *J. Polym. Sci. Polym. Lett. Edn.* 1976, 14, 549-554; D. J. Liaw, et al., *J. Appl. Polym. Sci.* 1992, 45, 61-70—each incorporated herein by reference in its entirety) (Scheme 1). $^{31}$P NMR signal for monomer Z 4, ZA 9, ZDAN 11, PZ 5, and PZA 6 appeared at δ31.01, 28.02, 17.41, 31.13 and 25.35 ppm, respectively. The upfield shift of P signal in ZDAN 11 is attributed to the presence of negatively charged oxygens which increase the electron density around P.

Perkin Elmer Elemental Analyzer Series II Model 2400 instrument was used to carry out elemental analysis. A Perkin Elmer 16F PC FTIR spectrometer was used to record IR spectra. The $^{13}$C, $^1$H and $^{31}$P NMR spectra have been measured in D$_2$O on a JEOL LA 500 MHz spectrometer. The $^1$H HOD signal at δ 4.65 and $^{13}$C peak of dioxane at δ 67.4 were used as internal standards. $^{31}$P was referenced with 85% H$_3$PO$_4$ in dimethyl sulfoxide. Ubbelohde viscometer was used to carry out viscosity measurements under N$_2$ to avoid prevent CO$_2$ absorption. A Sartorius pH Meter PB 11 was used for the potentiometric titrations. The temperature (25-800° C.) for the TGA, carried out in a thermal analyzer (STA 449F3), was increased at a rate of 15° C./min using air (flowing rate of 100 mL/min). An Agilent 1200 series instrument having a RI detector and PL aquagel-OH MIXED column helped to determine the molecular weights. The GPC measurements were performed using water flowing at a rate of 1.0 mL min) at 25° C. and a standard of polyethylene oxide/glycol.

As illustrated in FIG. 3, PZ 5 was observed to be stable up to around 225° C. as shown in the thermogravimetric analysis (TGA) curve. The first steep weight loss of 40% in the temperature range 225-360° C. range was attributed to the loss of sulfopropyl moiety, while the second gradual loss of 25% in the 360-800° C. range was due to decomposition of the phosphonate ester functionality and the release of H$_2$O, NO$_x$ and CO$_2$ gases (H. S. Martinez-tapia, et al., *J Solid State Chem.* 2000, 151, 122-129—incorporated by reference herein in its entirety). The remaining mass of 35% is attributed to P$_2$O$_5$.

Figure 4:
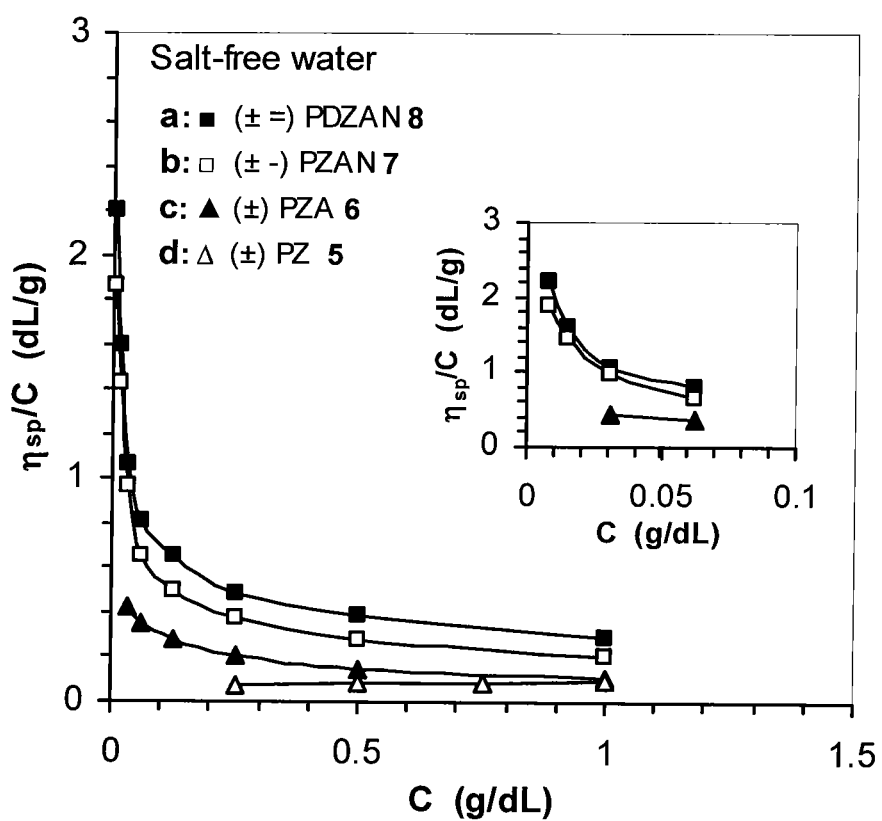
FIG. 4 shows a diagram demonstrating the viscosity behavior in salt-free water of different polymers.
Figure 5:
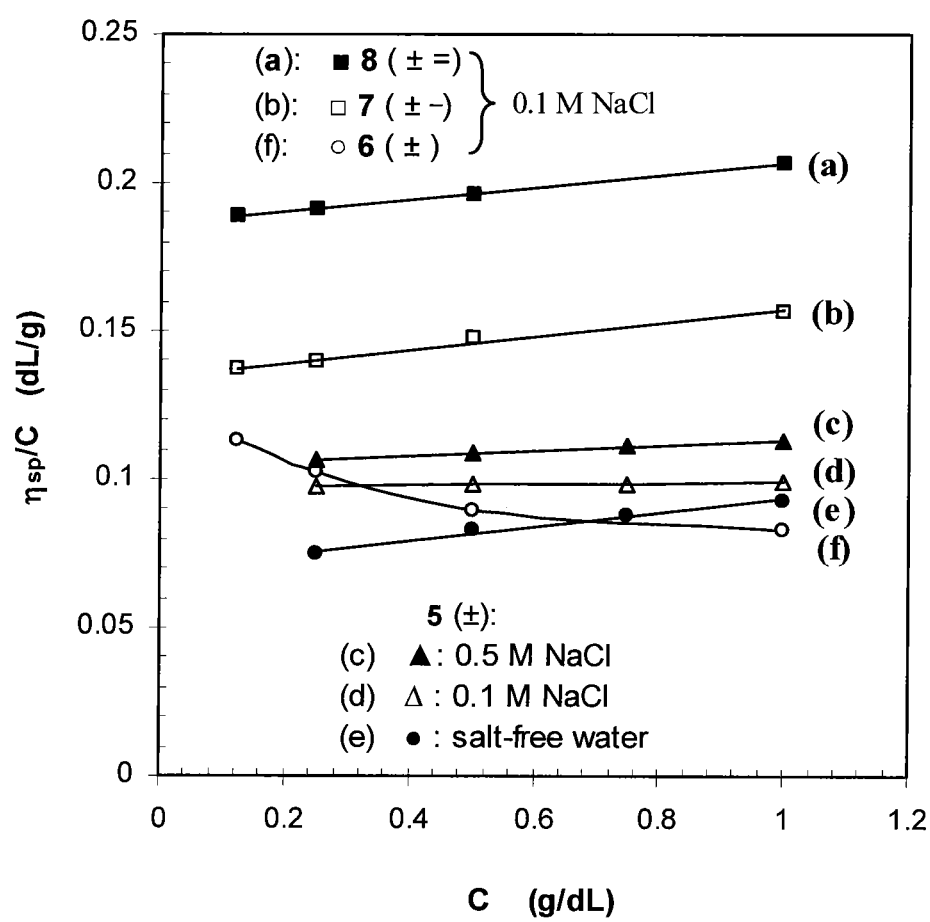
FIG. 5 shows a diagram demonstrating the viscosity behavior in 0.1 M NaCl of different polymers.

FIG. 4 illustrates the viscosity behavior in salt-free water of: (a) ■ (±=) PZDAN 8, (b) □ (±−) PZAN 7, (c) ▲ (±) PZA 6 and (d) Δ (±) PZ 5 using an Ubbelohde Viscometer at 30° C. (All polymers are derived from entry 3, Table 1). [Inset describes the viscosity plots of 6-8 in the higher dilution range]. FIG. 5 illustrates the viscosity behavior in 0.1 M NaCl of: (a) ■ (±=) PZDAN 8, (b) □ (±−) PZAN 7, (±) PZ 5 in (c) ▲ 0.5 M NaCl, (d) Δ 0.1 M NaCl, (e) ● in salt-free water and (f) ○ (±) PZA 6 in 0.1 M NaCl using an Ubbelohde Viscometer at 30° C. (all polymers are derived from entry 3, Table 1). FIG. 4 and FIG. 5 display the viscosity plots, as examined by the Huggins equation: $\eta_{sp}/C=[\eta]+k[\eta]^2C$, for the polymers 5-8 having identical number of repeating units. The intrinsic viscosity [η] of PZ 5 in salt-free water, 0.1 M and 0.5 M NaCl was measured to be 0.0700, 0.0968 and 0.104, respectively. With increasing NaCl concentration an increase in the intrinsic viscosity explains the antipolyelectrolyte behavior of PZ 5. The viscosity values of (±) PZ 5, (±) PZA 6, (±−) PZAN 7, (±=) PZDAN 8 in 0.1 M NaCl were found to be increasing in the order: 5<6<7<8. All the polymers have the common trait of having a zwitterionic group whereas 7 and 8 have in addition, an anionic and dianionic functionalities. The highest viscosity values of (±=) PZDAN 8 is attributed to the increased repulsion among the anionic charges leading to the expansion of the polymer backbone. Note that the viscosity plot of 6 is typical of polyelectrolytes i.e. concave upwards: Progressive dissociation of the —PO$_3$H$_2$ (pK$_a$: 2.83) in 6 leads to an increase in the incorporation of anionic and fractions —PO$_3$H$^-$ in the polymer backbone Based on the pK$_a$ value of 2.83 in 0.1 M NaCl (vide infra), the extent of dissociation of —PO$_3$H$_2$ in 1, 0.5, 0.25 and 0.125 g/dL solutions has been determined to be 20, 27, 36, and 46, respectively. Note that the viscosity plot of 7 remains linear since the weak acidity of —PO$_3$H$^-$ (pK$_a$: 8) in 7 leads to an insignificant level of dissociation: the percent dissociation remains 0.05-0.13 in the concentration range 1-0.125 g/dL.

Inspection of FIG. 4 and FIG. 5 reveals that both the viscosity plots of (±) PZA 6 in salt-free water and 0.1 M NaCl are concave upwards thereby indicating its polyelectrolyte nature. The polyelectrolyte effect is more pronounced in the former medium even though the —PO$_3$H$_2$ pK$_a$ value of 3.26 in salt-free water is higher than that of 2.83 in 0.1 M NaCl. The percent dissociation of —PO$_3$H$_2$ in (±) PZA 6 to (±) —PO$_3$H$^-$ in 1, 0.5, 0.25 and 0.125 g/dL solutions in salt-free water is calculated to be 13, 18, 24, and 32, respectively, which are less than that in 0.1 M NaCl. Increased dissociation in 0.1 M NaCl and repulsion among the anions lead to an increase in the viscosity values. However, the lower viscosity values in 0.1 M NaCl is attributed to the greater contraction of the polymer chain by shielding of the (±)—PO$_3$H$^-$ anions by Na$^+$ ions (polyelectrolyte effect) than the expansion as a consequence of more effective shielding of the positive nitrogens resulting in an overall net negative charge on the zwitterionic portion (anti-polyelectrolyte effect) (K. Nishida, et al., *Polymer* 2002, 43, 1295-1300—incorporated herein by reference in its entirety).

Conversion of (±) PZA 6 by addition of 0.5, 1.0, 1.5, and 2 equivalents of NaOH to 1:1 (±) PZA 6/(PZAN) (±−) 7, (PZAN) (±−) 7, 1:1 (PZAN) (±−) 7/(PZDAN) (±=) 8, and (PZDAN) (+=) 8, respectively, results in the increase in viscosity value as a result of increasing concentration of the anionic portions. The anionic groups thus dominate the viscosity behavior.

Developed to interpret the solution behavior of charge symmetric or asymmetric polyampholytes, the solution behavior of the above polymers can also be described mathematically (R. Everaers, et al., *Europhys. Lett.* 1997, 37, 275-280; F. Candau, et al., *Polyampholytes (Properties in Aqueous Solution)*, J. C. Salamone. Ed.; CRC Press: Boca Raton, Fla. 1996, 7, 5462-5476; J. Wittmer, et al., *Europhys. Lett.* 1993, 24, 263-268—each incorporated herein by reference in its entirety) in terms of:

$$v^* = -\frac{\pi(fI_B)^2}{\kappa_S} + \frac{4\pi I_B \Delta f^2}{\kappa_S^2} \qquad (4)$$

where f is the total fraction of charged monomers, Δf is the charge imbalance, $I_B$ is the Bjerrum length, and $\kappa_S$ is the Debye-Huckel screening parameter. The first and second term in eq 4 describes the shielding of the attractive polyampholytic and Coulombic repulsive interactions, interactions, respectively. The negative or positive electrostatic excluded volume (v*) indicates respective contraction to a coiled polymer chain or its expansion to a semicoil. For the electroneutral (±) PZA 5, the second term vanishes as a result of Δf=0, the solution behavior is then be described by the first term describing the screening of the attractive polyampholytic interactions that results in a negative excluded volume.

For (±) PZA 6 in equilibrium with its dissociated form (±−), (PZAN) (±−) 7, and (PZDAN) (±=) 8 Δf≠0; the charge imbalance is maximum for (PZDAN) (±=) 8. The greater dominance of the second term in eq 4 results in higher positive excluded volume and viscosity. The relative importance of the first and second terms of eq 4 dictates the solution behavior. As the salt (NaCl) concentration increases (from 0 to 0.1 N), the magnitude of the first and second term increases and decreases, respectively. The anionic (−) and zwitterionic (±) groups experience opposite influence in the presence of salt; NaCl helps the anionic portions to coil up (Δf becomes less as a result of shielding) and the zwitterionic portions to expand (Δf becomes more as a result of more effective shielding of positive nitrogens by Cl⁻ ions that that of —O⁻ by Na⁺ ions). The increased percent dissociation of —PO₃H₂ in PZA 6 associated with the decrease in polymer concentration increases the progressive importance of the second term (eq 4). This is indeed corroborated by the observed increase in the viscosity values with decreasing polymer concentration (FIG. 4). Note that (PZAN) (±−) 7 may be considered as an alternating anionic-zwitterionic polymer since its behavior is akin to that of an alternating anionic-zwitterionic copolymer derived from p-vinylbenzene sulfonate and o-vinyl-N-(3-sulfopropyl)pyridine (J. C. Salamone, et al., *J. Macromol. Sci-Chem.* A 1991, 28, 885-895—incorporated herein by reference in its entirety).

Figure 6:
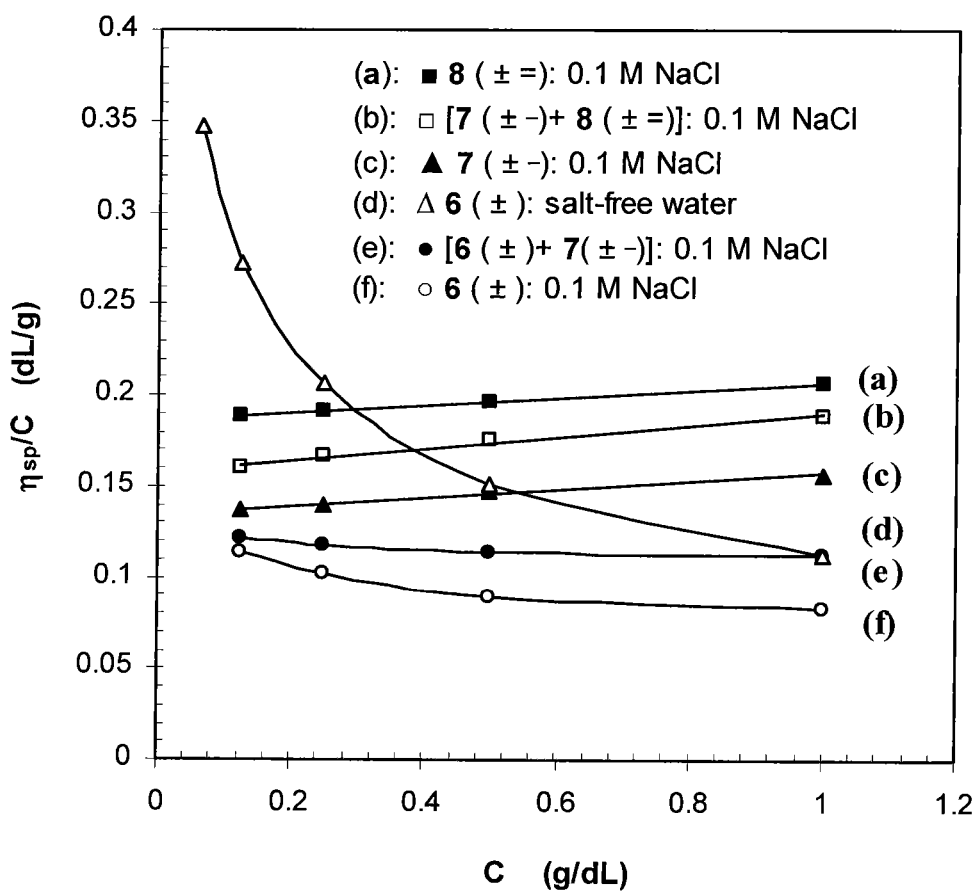
FIG. 6 shows a diagram demonstrating the viscosity behavior in 0.1 M NaCl of different polymers.

Using an Ubbelohde Viscometer at 30° C., FIG. 6 illustrates the viscosity behavior in 0.1 M NaCl of: (a) ■ (±=) PZDAN 8, (b) ☐ 1:1 (±−) PZAN 7/(±=) PZDAN 8; (c) ▲ (±−) PZAN 7 (d) Δ (±) PZA 6 in salt-free water, (e) ● 1:1 (±) PZA 6/(±−) PZAN 7 in 0.1 M NaCl and (1) ○ (±) PZA 6 in 0.1 M NaCl. (all polymers are derived from entry 3, Table 1).

Figure 7:
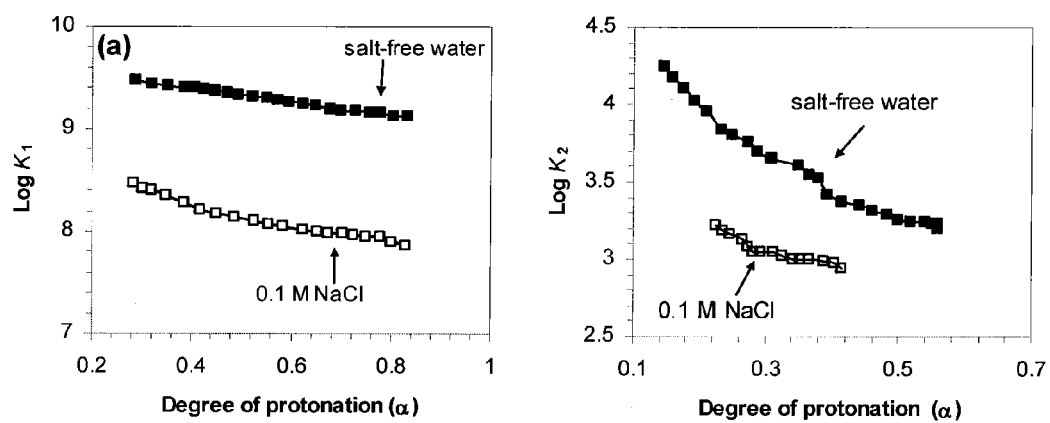
FIG. 7 shows a plot for the apparent (a) log $K_1$ versus degree of protonation (α) and (b) log $K_2$ versus (α) for PZA 6 in salt-free water and 0.1 M NaCl.

FIG. 7 illustrates a plot for the apparent (a) log $K_1$ versus degree of protonation (α) (entry 3, Table 3) and (b) log $K_2$ versus α) for PZA 6 in salt-free water and 0.1 M NaCl (entry 3, Table 4). In FIG. 7, both the basicity constant log $K_1$ and log $K_2$ for the respective protonation of the —PO₃²⁻ (in 8) and —PO₃H⁻ (in 7) in salt-free water and 0.1 M NaCl are of "apparent" (R. Barbucci, et al., *Macromolecules* 1983, 16, 456-462—incorporated herein by reference in its entirety) nature (Scheme 1), which reveals a decrease in log K with the increase in degree of protonation (α). A decrease in the basicity of —PO₃²⁻ (owing to gradual change of (±=) groups to (±−)) with the increase in a is a direct consequence of a decrease in the electrostatic field force that encourages protonation. For log $K_1$, a slightly stronger polyelectrolyte effect is observed in 0.1 M NaCl than in salt-free water as confirmed by the higher n value in the former medium (of 1.53 vs. 1.33) (Table 3). Note that for 11, n values of 1 for both log $K_1$ and log $K_2$ in salt-free water as well as 0.1 M NaCl is expected for a small monomer molecule. Table 3, as illustrated below, demonstrates the details for the details for the first protonation of monomer ZDAN ($Z^{±=}$) 11 and polymer PZDAN 8 ($Z^{±=}$) at 23° C. in Salt-Free Water and 0.1 M NaCl.

TABLE 3

Details for the First Protonation of Monomer ZDAN ($Z^{±=}$) 11 and Polymer PZDAN 8 ($Z^{±=}$) at 23° C. in Salt-Free Water and 0.1M NaCl

| run | $ZH_2^±$ or $Z^{±-}$ (mmol) | $C_T^a$ (mol dm⁻³) | α-range | pH-range | Points[b] | Log $K_1^{oc}$ $n_1^c$ | | $R^2$,[d] |
|---|---|---|---|---|---|---|---|---|
| | | | Polymer 6 in Salt-Free water | | | | | |
| 1 | 0.2361 ($ZH_2^±$) | −0.1016 | 0.88-0.20 | 8.25-10.11 | 20 | 9.33 | 1.29 | 0.9986 |
| 2 | 0.2944 ($ZH_2^±$) | −0.1016 | 0.90-0.26 | 8.04-9.93 | 18 | 9.29 | 1.36 | 0.9976 |
| 3 | 0.3826 (6: $ZH_2^±$) | −0.1016 | 0.83-0.29 | 8.42-9.87 | 22 | 9.33 | 1.34 | 0.9989 |
| Average | | | | | | 9.32 (2) | 1.33 (4) | |

$\text{LogK}_1^e = 9.32 + 0.33\log[(1-\alpha)/\alpha]$ For the reaction: $Z^{±=} + H^+ \overset{K_I}{\rightleftharpoons} ZH^{±-}$

| | | | Polymer 6 in 0.1M NaCl | | | | | |
|---|---|---|---|---|---|---|---|---|
| 1 | 0.2323 ($ZH_2^±$) | −0.1016 | 0.86-0.18 | 7.03-9.25 | 16 | 8.17 | 1.49 | 0.9935 |
| 2 | 0.2637 ($ZH_2^±$) | −0.1016 | 0.85-0.17 | 7.10-9.30 | 18 | 8.23 | 1.58 | 0.9920 |
| 3 | 0.2950 (6: $ZH_2^±$) | −0.1016 | 0.83-0.28 | 7.18-8.88 | 20 | 8.18 | 1.52 | 0.9910 |
| Average | | | | | | 8.19 (3) | 1.53 (5) | |

$\text{LogK}_1^e = 8.19 + 0.53\log[(1-\alpha)/\alpha]$ For the reaction: $Z^{±=} + H^+ \overset{K_I}{\rightleftharpoons} ZH^{±-}$ TABLE 3-continued Details for the First Protonation of Monomer ZDAN ($Z^{\pm=}$) 11 and Polymer PZDAN 8 ($Z^{\pm=}$) at 23° C. in Salt-Free Water and 0.1M NaCl

| run | $ZH_2^\pm$ or $Z^{\pm=}$ (mmol) | $C_T{}^a$ (mol dm$^{-3}$) | α-range | pH-range | Points[b] | Log $K_1{}^{oc}$ | $n_1{}^c$ | $R^2$,[d] |
|---|---|---|---|---|---|---|---|---|
| Monomer 11 in Salt-Free water | | | | | | | | |
| 1 | 0.1845 (11: $Z^{\pm=}$) | +0.1222 | 0.20-0.86 | 8.18-6.70 | 15 | 7.50 | 1.04 | 0.9908 |
| 2 | 0.2577 ($Z^{\pm=}$) | +0.1222 | 0.24-0.90 | 8.04-6.61 | 17 | 7.54 | 1.04 | 0.9875 |
| 3 | 0.3361 ($Z^{\pm=}$) | +0.1222 | 0.22-0.87 | 8.04-6.72 | 18 | 7.55 | 1.05 | 0.9845 |
| Average | | | | | | 7.53 | 1.04 (1) | |

$\text{Log} K_1^e = 7.53$ For the reaction: $Z^{\pm=} + H^+ \overset{K_l}{\rightleftharpoons} ZH^{\pm-}$

| | | | Monomer 11 in 0.1M NaCl | | | | | |
|---|---|---|---|---|---|---|---|---|
| 1 | 0.2206 (11: $Z^{\pm=}$) | +0.1222 | 0.22-0.89 | 7.70-6.17 | 16 | 7.12 | 1.03 | 0.9927 |
| 2 | 0.2621 ($Z^{\pm=}$) | +0.1222 | 0.19-0.89 | 7.85-6.20 | 18 | 7.11 | 1.03 | 0.9880 |
| 3 | 0.3062 ($Z^{\pm=}$) | +0.1222 | 0.16-0.88 | 8.01-6.29 | 20 | 7.13 | 1.04 | 0.9920 |
| Average | | | | | | 7.12 (1) | 1.03 (1) | |

$\text{Log} K_1^e = 7.12$ For the reaction: $Z^{\pm=} + H^+ \overset{K_l}{\rightleftharpoons} ZH^{\pm-}$

[a](−)ve and (+)ve values describe respective titrations with NaOH and HCl).
[b]Number of data points.
[c]Standard deviations in the last digit are given under the parentheses.
[d]R = Correlation coefficient.
[e]log $K_1$ = log $K_1^o$ + ($n_1$ − 1) log [(1 − α)/α].

For log $K_2$, a considerably stronger polyelectrolyte effect in salt-free water is attributed to its having a greater n value of 2.16 compared to 1.60 in 0.1 M NaCl (Table 4). The gradual increase in α leads to a progressive transformation of the negative charge density in (±−) PZAN 7 to electroneutral (±) PZA 6 whose collapsed conformation make it difficult for the protons to access the basic sites. Table 4, as illustrated below, demonstrates the details for the second protonation of monomer ZDAN ($Z^{\pm=}$) 11 and polymer PZDAN 8 ($Z^{\pm=}$) at 23° C. in Salt-Free Water and 0.1 M NaCl.

TABLE 4

Details for the Second Protonation of Monomer ZDAN ($Z^{\pm=}$) 11 and Polymer PZDAN 8 ($Z^{\pm=}$) at 23° C. in Salt-Free Water and 0.1M NaCl

| run | $ZH_2^\pm$ or $Z^{\pm=}$ (mmol) | $C_T{}^a$ (mol dm$^{-3}$) | α-range | pH-range | Points[b] | Log $K_2{}^{oc}$ | $n_2{}^c$ | $R^2$,[d] |
|---|---|---|---|---|---|---|---|---|
| Polymer 6 in Salt-Free water | | | | | | | | |
| 1 | 0.2361 ($ZH_2^\pm$) | −0.1016 | 0.52-0.17 | 3.29-4.86 | 20 | 3.29 | 2.21 | 0.9942 |
| 2 | 0.2944 ($ZH_2^\pm$) | −0.1016 | 0.51-0.19 | 3.17-4.56 | 22 | 3.21 | 2.11 | 0.9962 |
| 3 | 0.3826 (6: $ZH_2^\pm$) | −0.1016 | 0.56-0.15 | 3.10-5.02 | 24 | 3.28 | 2.16 | 0.9925 |
| Average | | | | | | 3.26 (4) | 2.16 (5) | |

$\text{Log} K_2^e = 3.26 + 1.16\log[(1-\alpha)/\alpha]$ For the reaction: $Z^{\pm-} + H^+ \overset{K_2}{\rightleftharpoons} ZH_2^\pm$

| | | | Polymer 6 in 0.1M NaCl | | | | | |
|---|---|---|---|---|---|---|---|---|
| 1 | 0.2323 ($ZH_2^\pm$)[f] | −0.1016 | 0.47-0.27 | 2.87-3.47 | 16 | 2.79 | 1.52 | 0.9975 |
| 2 | 0.2637 ($ZH_2^\pm$)[f] | −0.1016 | 0.51-0.31 | 2.82-3.40 | 18 | 2.84 | 1.65 | 0.9906 |
| 3 | 0.2950 (6: $ZH_2^\pm$) | −0.1016 | 0.41-0.23 | 3.09-3.76 | 15 | 2.85 | 1.63 | 0.9869 |
| Average | | | | | | 2.83(3) | 1.60(7) | |

$\text{Log} K_2^e = 2.83 + 0.60\log[(1-\alpha)/\alpha]$ For the reaction: $Z^{\pm-} + H^+ \overset{K_2}{\rightleftharpoons} ZH_2^\pm$

| | | | Monomer 11 in Salt-Free water | | | | | |
|---|---|---|---|---|---|---|---|---|
| 1 | 0.1845 (11: $Z^{\pm=}$) | +0.1222 | 0.15-0.52 | 3.55-2.73 | 19 | 2.75 | 1.02 | 0.9849 |
| 2 | 0.2577 ($Z^{\pm=}$) | +0.1222 | 0.16-0.58 | 3.47-2.61 | 18 | 2.72 | 0.984 | 0.9926 |
| 3 | 0.3361 ($Z^{\pm=}$) | +0.1222 | 0.17-0.62 | 3.50-2.57 | 20 | 2.75 | 1.05 | 0.9896 |
| Average | | | | | | 2.74 (2) | 1.02 (3) | |

$\text{Log} K_2^e = 2.74$ For the reaction: $Z^{\pm=} + H^+ \overset{K_2}{\rightleftharpoons} ZH_2^\pm$ TABLE 4-continued Details for the Second Protonation of Monomer ZDAN ($Z^{+-}$) 11 and Polymer
PZDAN 8 ($Z^{+-}$) at 23° C. in Salt-Free Water and 0.1M NaCl

| run | $ZH_2^+$ or $Z^{+-}$ (mmol) | $C_T{}^a$ (mol dm$^{-3}$) | α-range | pH-range | Points$^b$ | Log $K_2{}^{oe}$ | $n_2{}^c$ | $R^2$, $^d$ |
|---|---|---|---|---|---|---|---|---|
| | | | Monomer 11 in 0.1M NaCl | | | | | |
| 1 | 0.2206 (11: $Z^{+-}$) | +0.1222 | 0.15-0.52 | 3.71-2.91 | 16 | 2.91 | 0.993 | 0.9929 |
| 2 | 0.2621 ($Z^{+-}$) | +0.1222 | 0.18-0.52 | 3.55-2.79 | 17 | 2.84 | 1.06 | 0.9918 |
| 3 | 0.3062 ($Z^{+-}$) | +0.1222 | 0.17-0.64 | 3.65-2.70 | 19 | 2.94 | 0.990 | 0.9936 |
| Average | | | | | | 2.90 (5) | 1.01 (4) | |

Log$K_2^e$ = 2.90 For the reaction: $Z^{+-} + H^+ \overset{K_2}{\rightleftharpoons} ZH_2^{\pm}$ $^a$(-)ve and (+)ve values describe respective titrations with NaOH and HCl,.
$^b$data points from titration curve.
$^c$Standard deviations in the last digit are given under the parentheses.
$^d$R = Correlation coefficient.
$^e$log $K_i$ = log $K_1{}^o$ + (n – 1) log [(1 – α)/α].
$^f$titration was carried out in the presence of 1.5 mL of 0.1222M HCl to attain the required values of the α.

Figure 8:
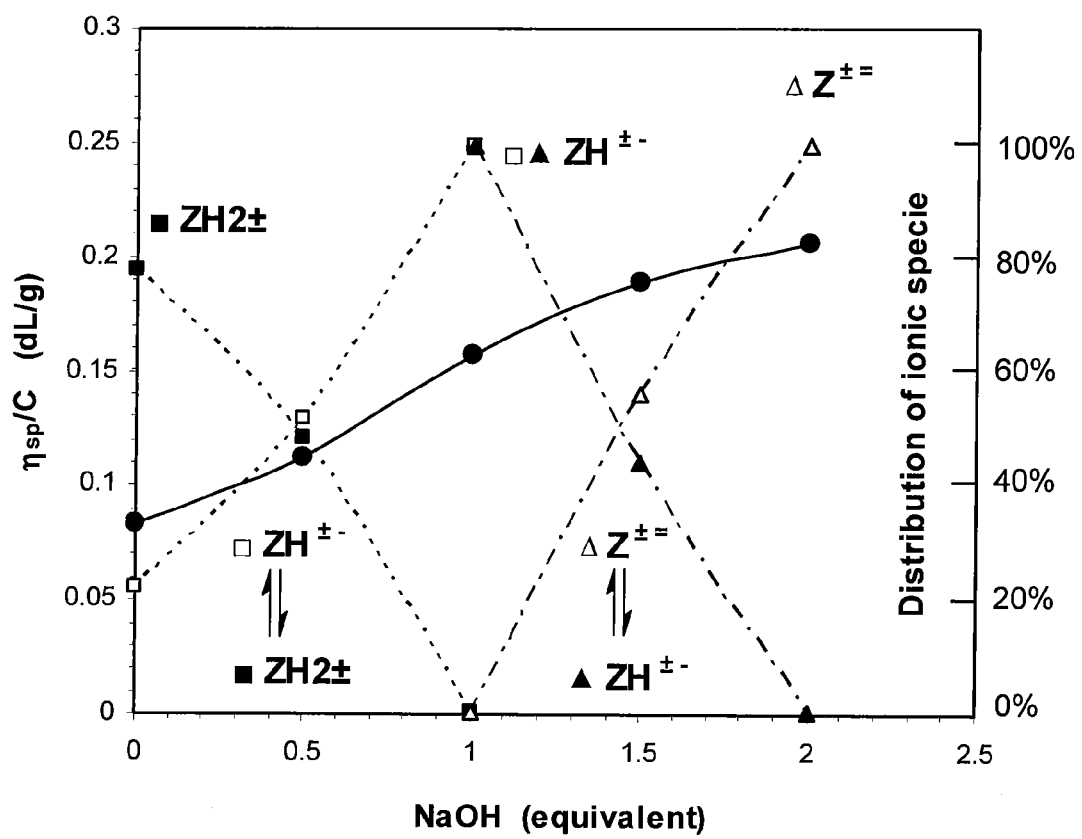
FIG. 8 shows a graph demonstrating the reduced viscosity ($\eta_{sp}/C$) at 30° C. of a solution of polymer PZA 6 in 0.1 N NaCl.

FIG. 8 illustrates a graph of reduced viscosity ($\eta_{sp}/C$) at 30° C. of a 0.0293 M (i.e. 1 g/dL) solution of polymer PZA 6 in 0.1 N NaCl (●) versus equivalent of added NaOH at 23° C. Distribution curves (dashed lines) of the various ionized species calculated using eq 2 and pH of the solutions in 0.1 N NaCl at 23° C. A viscometric titration of a 0.0293 M (i.e. 1 g/dL) solution of the polymer PZA 6 in 0.1 M NaCl solutions with NaOH at 23° C. is reported. FIG. 8 also shows the distribution curves of the specie $ZH_2^{\pm}$ (PZA 6), $ZH^{\pm-}$ (PZAN 7) and $Z^{+=}$ (PZDAN 9). The ionic specie were calculated from the basicity constants (vide supra) and pH values. With the increased addition of NaOH, the reduced viscosity increases as a result of increasing repulsions among the excess negative charges. Minimum viscosity is attributed to the presence of fully zwitterionic species 6. Increasing participation of zwitterionic/anionic and zwitterionic/dianionic species leads to gradual increase in the viscosity values.

Figure 9:
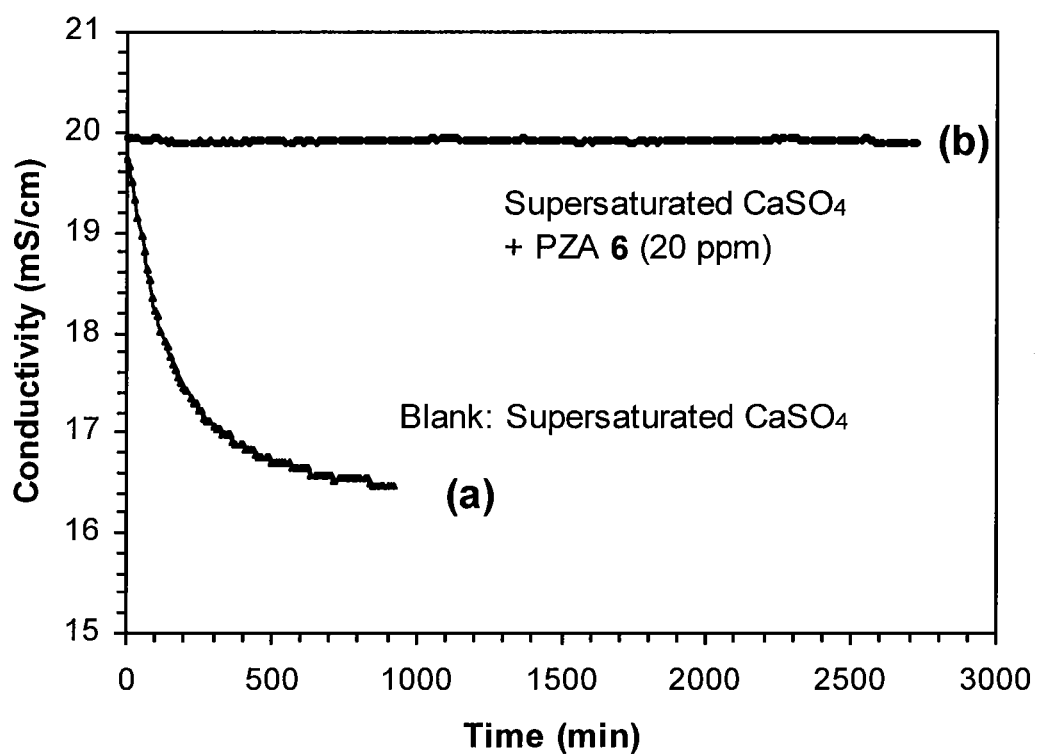
FIG. 9 shows the precipitation behavior of supersaturated solution of $CaSO_4$ in the presence (20 ppm) and absence of PZA 6.

As illustrated in FIG. 9, the precipitation behavior of supersaturated solution of $CaSO_4$ in the presence (20 ppm) and absence of PZA 6 is observed. A typical analysis (F. H. Butt, et al., *Desalination* 1995, 103, 189-198—incorporated herein by reference in its entirety) of brackish water and reject brine (i.e., concentrated brine, denoted as 1CB, at 70% recovery) from a Reverse Osmosis plant revealed the concentration of $Ca^{2+}$ as 281.2 and 866.7 ppm, respectively; while the corresponding concentration of $SO_4^{2-}$ to be 611 and 2,100 ppm.

The evaluation of the newly developed scale inhibitor was performed in solution containing $Ca^{2+}$ and $SO_4^{2-}$ by 3 times the concentration in the 1 CB. The 3 CB solutions containing 3×866.7 mg/L i.e., 2600 mg/L in $Ca^{2+}$ and 3×2100 mg/L i.e. 6300 mg/L in $SO_4^{2-}$ would be supersaturated as confirmed from solubility data of $CaSO_4$. Solutions containing $Ca^{2+}$ and $SO_4^{2-}$ ions equals to 6 times the concentrated brine (CB) were prepared by dissolving the calculated amount of $CaCl_2$ and $Na_2SO_4$, respectively, in deionized water. To a solution of 6 CB calcium chloride (60 mL) containing PZA 6 (40 ppm) in a round bottom flask at 40° C.±1° C. stirred at 300 rpm using a magnetic stir-bar, a preheated (40° C.) solution of 6 CB sodium sulfate (60 mL) was added quickly. Conductivity measurements of the resultant solution containing 20 ppm of PZA 6 were made at an interval of every 10 min initially to quantify the effectiveness of newly developed antiscalant PZA 6. The precipitation of $CaSO_4$ is indicated by a drop in conductivity. Visual inspection was carefully done to see any turbidity arising from precipitation.

Mineral scales of $CaCO_3$, $CaSO_4$, $Mg(OH)_2$, etc., polymeric silica, corrosion products, and suspended matter are hindrance to smooth functioning of desalination process. The ability of antiscalants to sequestrate polyvalent cations and alter the crystal morphology at the time of nucleation, inhibit growth rate of crystal formation (K. S. Spiegler, et al., *Principles of Desalination*, Part A, 2nd edn., Academic Press, New York, 1980—incorporated herein by reference in its entirety). poly(phosphate)s, organophosphates, and polyelectrolytes (J. S. Gill, *Desalination* 1999, 124, 43-50; H. David, S. Huila, et al., *Eng Chem Res* 2011, 50, 7601-7607—each incorporated herein by reference in its entirety) are the commonly used anionic antiscalants.

A number of polymeric antiscale agents are known. For example, U.S. Pat. Nos. 3,706,717; 3,879,288 and 4,518,511 disclose anionic polymers and methods of using them as antiscalants. However, the disclosed anionic polymers have relatively poor biodegradability. See also U.S. Pat. Nos. 5,064,563; 5,298,570; and 5,962,401. Anionic polymers carry a negative charge that is neutralized by positively charged counterions. The anionic polymer is generally considered to be the primary active ingredient in the polymeric antiscale agent, whereas the counterion is often regarded as a neutral or inactive species. Consequently, relatively low molecular weight counterions such as sodium and potassium were generally considered desirable in order to maximize the active solids content of the antiscale agent and/or to minimize costs. Organic counterions such as alkylammonium species were generally considered undesirable because their relatively high molecular weights reduced the active solids content of the antiscale agent, and because of their relatively high costs as compared to counterions such as sodium and potassium.

The antiscalant compositions may include one or more active ingredients including polycarboxylates, chelating agents, polyacrylates, polyphosphonates and polyphosphates (Sodium Hexa Meta Potassium), HEDP.

The feed water in the Reverse Osmosis process is split into product water and reject brine streams. Precipitation or scaling occurs as a result of supersaturation of dissolved salts and exceeding their solubility limits. Antiscalant behavior in the presence and absence of 20 ppm of PZA 6 was investigated using the precipitation behavior by conductivity measurements of a supersaturated solution of $CaSO_4$ containing 2600 ppm of $Ca^{2+}$ and 6300 ppm of $SO_4^{2-}$. A drop in conductivity is an indication of precipitation of CaSO4. Conductivity did not decrease for about 2700 min (45 h) thus registering ≈100% scale inhibition in the presence of a meager 20 ppm of PZA 6 (FIG. 9). Note that precipitation started immediately in the absence of antiscalant. The result thus certifies that this polymer is very much suitable for use in inhibiting calcium sulfate precipitation in RO plants.

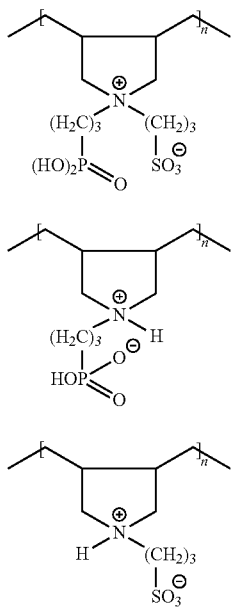

SCHEME 3 Zwitterionic cyclopolymers having phospho- and sulfobetaine motifs.

Scheme 3 illustrates the structures of the polyzwitterionic acid (PZA) (ZH$_2^\pm$) 6, a polymer 15 and a polymer 16. Polymer 15 includes the same repeating units of a five-membered heterocyclic ring having a nitrogen atom that is present in the (PZA) (ZH$_2^\pm$) 6. However, the nitrogen atom is bonded to a linking alkylene group, preferably a propylene group, and a hydrogen atom. The alkylene group is further bonded to a phosphonate group. Polymer 15 does not contain both the phosphonate and sulfonate groups that are present in the (PZA) (ZH$_2^\pm$) 6. Polymer 16 includes the same repeating units of a five-membered heterocyclic ring having a nitrogen atom that is present in the (PZA) (ZH$_2^\pm$) 6. However, the nitrogen atom is bonded to a linking alkylene group, preferably a propylene group, and a hydrogen atom. The alkylene group is further bonded to a sulfonate group. Polymer 16 does not contain both the phosphonate and sulfonate groups that are present in the (PZA) (ZH$_2^\pm$) 6.

The beneficial combined effect of both sulfonate and phosphonate groups in the same repeating unit in PZA 6 was proved as additive screening experiments based on visual inspection revealed that under the same conditions polymers having only sulfonate and phosphonate group (16) (I. W. Kazi, et al., Polym Eng Sci.: DOI 10.1002/pen.23548—incorporated herein by reference in its entirety) did not give effective inhibition. The system becomes cloudy within 1 h in the presence of 16, while polyphosphonate 15 performed better as CaSO$_4$ precipitate appeared after 35 h.

The synthesis and polymerization of Zwitterionic monomer 4 is described herein. The PZ 5 represents the first example of a Butler's cyclopolymer containing the dual functionality of phosphonate and sulfonate in the same repeating unit. The hydrolysis of the phosphonate ester groups resulted in the pH-responsive (±) PZA 6. The solution properties (including solubility behavior) that involved its conversion to (±−) PZAN 7 and (±=) PZDAN 8 all having identical degree of polymerization were studied. The solution properties were correlated to the type of charges and their densities on the polymer chain. The apparent basicity constants of the —PO$_3^{2-}$ and —PO$_3$H$^-$ group in (±−) PZAN 7 and (±=) PZDAN 8 have been determined. PZA 6 at a meager concentration 20 ppm imparted excellent inhibition of the formation of calcium sulfate scale and as such it can be used effectively as an antiscalant additive in Reverse Osmosis plant.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. A zwitterionic monomer having the following formula (4):

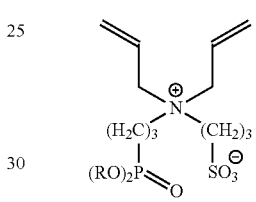

where R is a C$_1$ to C$_6$ alkyl group or C$_6$-C$_{12}$ aryl group.

2. The zwitterionic monomer of claim 1, wherein the alkyl groups R are both CH$_2$CH$_3$.

3. A polyzwitterion having the following formula (5):

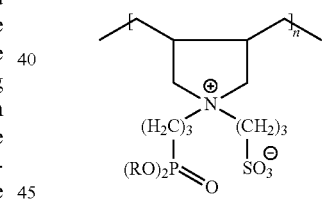

where R is a C$_1$ to C$_6$ alkyl group or a C$_6$-C$_{12}$ aryl group; and where n is an integer of 10 or greater.

4. The polyzwitterion of claim 3, wherein the alkyl group R is CH$_2$CH$_3$; and n is the number of repeating units in the range of 20-1,500.

5. A polyzwitterionic acid having the following formula (6):

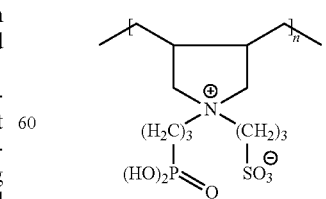

where n is an integer of 10 or greater.

6. The polyzwitterionic acid of claim 5, wherein n is the number of repeating units in the range of 20-1,500.

7. A poly(zwitterion/anion) having the following formula (7):

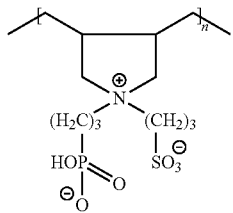

where n is an integer of 10 or greater.

8. The poly(zwitterion/anion) of claim 7, wherein n is the number of repeating units in the range of 20-1,500.

9. A poly(zwitterion/dianion) having the following formula (8):

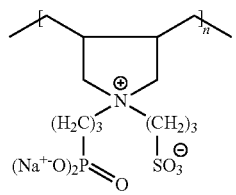

where n is an integer of 10 or greater.

10. The A poly(zwitterion/dianion) of claim 9, n is the number of repeating units in the range of 20-1,500.

11. A process for antiscaling, comprising:
   contacting a composition comprising the polyzwitterionic acid polymer of claim 5 with a surface comprising scale to remove the scale from the surface.

* * * * *